US010101325B2

(12) United States Patent
Sundrehagen

(10) Patent No.: US 10,101,325 B2
(45) Date of Patent: Oct. 16, 2018

(54) DETERMINATION METHOD FOR CALPROTECTIN AND THE USE OF CALPROTECTIN AS A PREDICTIVE MARKER FOR CARDIOVASCULAR DISEASE

(75) Inventor: Erling Sundrehagen, Oslo (NO)

(73) Assignee: SUNDREHAGEN, ERLING, DR., Medderud (SE)

( * ) Notice: Subject to any disclaimer, the term of this patent is extended or adjusted under 35 U.S.C. 154(b) by 1228 days.

(21) Appl. No.: 10/539,797

(22) PCT Filed: Dec. 22, 2003

(86) PCT No.: PCT/GB03/05607
§ 371 (c)(1),
(2), (4) Date: Dec. 19, 2005

(87) PCT Pub. No.: WO2004/057341
PCT Pub. Date: Jul. 8, 2004

(65) Prior Publication Data
US 2006/0134705 A1   Jun. 22, 2006

(30) Foreign Application Priority Data
Dec. 20, 2002 (GB) .................................. 0229747.1

(51) Int. Cl.
G01N 33/543 (2006.01)
G01N 33/68 (2006.01)
G01N 33/53 (2006.01)
C07K 16/02 (2006.01)

(52) U.S. Cl.
CPC ... *G01N 33/54346* (2013.01); *G01N 33/6893* (2013.01); *C07K 16/02* (2013.01); *G01N 33/5306* (2013.01); *G01N 33/54393* (2013.01); *G01N 2333/4727* (2013.01); *G01N 2800/32* (2013.01)

(58) Field of Classification Search
None
See application file for complete search history.

(56) References Cited

U.S. PATENT DOCUMENTS

| 4,287,202 | A | | 9/1981 | Horrobin | |
| 4,401,765 | A | * | 8/1983 | Craig et al. ................. | 436/533 |
| 4,480,042 | A | * | 10/1984 | Craig et al. ................. | 436/533 |
| 4,690,908 | A | * | 9/1987 | Mochida et al. ............ | 436/518 |
| 4,833,074 | A | | 5/1989 | Fagerhol et al. | |
| 5,455,160 | A | | 3/1995 | Fagerhol et al. | |
| 5,679,581 | A | * | 10/1997 | Miyazaki ......... | G01N 33/54313 436/164 |
| 5,776,348 | A | | 7/1998 | Dretler et al. | |
| 6,040,147 | A | | 3/2000 | Ridker et al. | |
| 7,011,952 | B2 | * | 3/2006 | Hageman et al. ........... | 435/7.21 |
| 2002/0168784 | A1 | | 11/2002 | Dag Bremnes et al. | |
| 2003/0166302 | A1 | * | 9/2003 | Shigenobu ............ | C08F 220/60 436/518 |

FOREIGN PATENT DOCUMENTS

| EP | 0 194 686 A1 | | 9/1986 | | |
| JP | 60 139621 A | | 7/1985 | | |
| WO | WO 89/08261 | | 9/1989 | | |
| WO | 98/20355 A | | 5/1998 | | |
| WO | 00/11479 A | | 3/2000 | | |
| WO | WO 01/02853 A2 | * | 1/2001 | ............ | G01N 33/48 |
| WO | 01/15744 A1 | | 3/2001 | | |
| WO | WO 01/94547 A2 | | 12/2001 | | |
| WO | WO 2004/057341 A2 | * | 7/2004 | ............ | G01N 33/68 |

OTHER PUBLICATIONS

The Merck Manuals Online Medical Library, table of contents for the section "Heart and Blood Vessel Disorders", retrieved from http://www.merck.com/mmhe/sec03.html on Oct. 16, 2008.*
Yui et al. "Calprotectin (S100A8/S100A9), an Inflammatory Protein Complex from Neutrophils with a Broad Apoptosis-Inducing Activity"; Biol. Pharm. Bull. 26(6) 753-760 (2003).*
LaBaer et al., Journal of Proteome Research (2005), vol. 4, pp. 1053-1059.*
Mayeux et al. "Biomarkers: Potential uses and Limitations"; NeuroRx (2004); vol. 1, pp. 182-188.*
Definition of the term 'Antiserum' from Wikipedia, retrieved from http://en.wikipedia.org/wiki/Antiserum on Sep. 25, 2013, one page.*
Newman et al. "Serum cystatin C measured by automated immunoassay: A more sensitive marker of changes in GFR than serum creatinine", Kidney International, vol. 47 (1995), pp. 312-318.*
Abcam, "A comparison between polyclonal and monoclonal", two pages, retrieved from http://docs.abcam.com/pdf/antibody-guide/a-comparison-between-polyclonal-and-monoclonal.pdf on Jul. 9, 2015.*
Thakkar et al. "Stabilization of Turbidimetric Immunoassay by Covalent Coupling of Antibody to Latex Particles" Clin. Chem. 37/7, 1248-1251 (1991).*
Price et al. "Development and validation of a particle-enhanced turbidimetric immunoassay for C-reactive protein" Journal of Immunological Methods vol. 99, Issue 2, May 20, 1987, pp. 205-211.*
Wei et al. "An improved automated immunoassay for C-reactive protein on the Dimension clinical chemistry system" Journal of Automated Methods & Management in Chemistry, vol. 22, No. 5 (Sep.-Oct. 2000) pp. 125-131.*
Kyhse-Andersen et al. "Serum Cystatin C, Determined by a Rapid, Automated Particle-Enhanced Turbidimetric Method, Is a Better Marker than Serum Creatinine for Glomerular Filtration Rate" Clin. Chem. 40/10, 1921-1926 (1994).*
Newman, D. "Cystatin C" Ann Clin Biochem 2002; 39: 89-104.*
Nilsen et al. "A new turbidimetric immunoassay for serum calprotectin for fully automated clinical analysers" Journal of Inflammation (2015), 8 pages, doi: 10.1186/s12950-015-0090-3 (Year: 2015).*

(Continued)

Primary Examiner — Christine Foster
(74) Attorney, Agent, or Firm — Bacon & Thomas, PLLC

(57) ABSTRACT

An assay method for the detection of potential for CVD or propensity to CVD in a human or non-human animal subject, said method comprising assessing the concentration of calprotectin in a calprotectin-containing sample taken from said subject.

13 Claims, 7 Drawing Sheets

(56) References Cited

OTHER PUBLICATIONS

R. Vliegenthart, M. Oudkerk, B. Song, D.A.M. van der Kulp, A. Hofman and J.C.M. Witteman, "Coronary calcification detected by electron-beam computed tomography and myocardial infarction", The Rotterdam Coronary Calcification Study, European Heart Journal, Oct. 2002, vol. 23, issue 20, pp. 1596-1603.
Carlos Iribarren, Stephen Sidney, Barbara Sternfeld and Warren S. Browner, "Calcification of the Aortic Arch Risk Factors and Association with Coronary Heart Disease, Stroke, and Peripheral Vascular Disease", JAMA, Jun. 7, 2000, vol. 283, No. 21, pp. 2810-2815.
Yadon Arad, Louise A. Spadaro, Ken Goodman, David Newstein and Alan D. Guerci, "Prediction of Coronary Events with Electron Beam Computed Tomography", Journal of American College of Cardiology, Oct. 2000, vol. 36, No. 4, pp. 1253-1260.
Paolo Raggi, Tracy Q. Callister, Bruce Cooil, Zuo-Xiang He, Nicholas J. Lippolis, Donald J. Russo, Alan Zelinger and John J. Mahmarian, "Identification of Patients at Increased Risk of First Unheralded Actue Myocardial Infarction by Electron-Beam Computed Tomography", Circulation, Feb. 29, 2000, pp. 850-855.
Lawrence F. Bielak, John A. Rumberger, Patrick F. Sheedy II, Robert S. Schwartz and Patricia A. Peyser, "Probabilistic Model for Prediction of Angiographically Defined Obstructive Coronary Artery Disease Using Electron Beam Computed Tomography Calcium Score Strata", Circulation, Jul. 25, 2000, pp. 380-385.
Nathan D. Wong, Jeffrey C. Hsu, Robert C. Detrano, George Diamond, Harvey Eisenberg and Julius M. Gardin, "Coronary Artery Calcium Evaluation by Electron Beam Computed Tomography and its Relation to New Cardiovascular Events", The American Journal of Cardiology, vol. 86, Sep. 1, 2000, pp. 495-498.
Rozemarijn Vliegenthart, Monika Hollander, Monique M.B. Breteler, Deirdre A.M. van der Kuip, Albert Hofman, Matthijs Oudkerk and Jacqueline C. M. Witteman, "Stoke is Associated with Coronary Calcification as Detected by Electron-Beam CT, The Rotterdam Coronary Calcification Study", Stroke, Feb. 2002, pp. 462-465.
Clinical Cardiology: Pathophysiology of Acute Ischemic Syndromes, Abstract, 69th Scientific Sessions, AHA, New Orleans, Nov. 13, 1996.
B. Johne, M. K. Fagerhol, T. Lyberg, H. Prydz, P. Brandtzaeg, C.F. Naess-Andresen, I. Dale, "Functional and clinical aspects of the myelomonocyte protein calprotectin", Molecular Pathology, Jun. 1997, vol. 50, No. 3, pp. 113-123.
Information Sheet Supplied with Eurospital® Test—Calprest®.
Lagasse E. et al., "Mouse MRP8 and MRP14, Two Intracellular Calcium-binding Proteins Associated with the Development of the Myeloid Lineage" Blood, W.B. Saunders, Philadelphia, VA, vol. 79, 1992, pp. 1907-1915, XP000653772.
Pechkovsky D. V. et al., "Calprotectin (MRP8/14 Protein Complex) Release During Mycobacterial Infection in vitro and in vivo." FEMS Immunology and Medical Microbiology, Netherlands, Sep. 2000, vol. 29, No. 1 ,pp. 27-33, XP002279820.
Kido Jun-Ichi et al., "Calprotectin in Gingival Crevicular Fluid Correlates with Clinical and Biochemical Markers of Periodontal Disease", Journal of Clinical Periodontology, Copenhagen, DK, vol. 26, No. 10, 1999, pp. 653-657, XP009030803.
Semb A. G. et al., "Cardiac Surgery and Distribution of the Leukocyte L1 Protein-Calprotectin", European Journal of Cardio-Thoracic Surgery, Springer Verlag, Berlin, DE, vol. 5, No. 7, 1991, pp. 363-367, XP009030797.
Saatvedt K. et al., "Release of Interleukin-8 and Calprotectin During and after Paediatric Cardiopulmonary Bypass with and without Ultrafiltration", Scandinavian Journal of Thoracic and Cardiovascular Surgery, Stockholm, SE, vol. 30, No. 2, 1996, pp. 53-59, XP009030799.
Moen O. et al., "Roller and Centrifugal Pumps Compared in Vitro with Regard to Haemolysis, Granulocyte and Complement Activation", Perfusion, vol. 9, No. 2, Mar. 1994, pp. 109-117, XP009030798.
Brun J.G. et al., "Effects of Human Calprotectin (L1) on in vitro Immunoglobulin Synthesis" Scandinavian Journal of Immunology, Blackwell Science Publ., vol. 40, No. 6, Dec. 1994, pp. 675-680, XP009030805.
K. Arvesen, et al., "Calprotectin: A Novel Plasma Marker of Granulocyte Activation in Acute Coronary Syndrome" European Society of Cardiology, Birmingham—United Kingdom, Circulation, vol. 94 (8), Aug. 25-29, 1996, pp. 3015.
F. Haverkate, et al., "C-reactive protein and cardiovascular disease", Fibrinolysis and Proteolysis, 1997, vol. 11, No. 1, pp. 133-134.
Lewis H. Kuller, et al., "Relation of C-Reactive Protein and Coronary Heart Disease in the MRFIT Nested Case-Control Study", American Journal of Epidemiology, 1996, vol. 144, No. 6, pp. 537-547.
Frits Haverkate, et al., "Production of C-reactive protein and risk of coronary events in stable and unstable angina", The Lancet, Feb. 15, 1997, vol. 349, pp. 462-466.
Shih-Jen Hwang, PhD., et al., "Circulating Adhesion Molecules VCAM-1, ICAM-1, and E-selectin in Carotid Atheroschlerosis and Incident Coronary Heart Disease Cases—The Atherosclerosis Risk in Communities (ARIC) Study", Circulation, Dec. 16, 1997, vol. 96, No. 12, pp. 4219-4225.
Simon G. Thompson, et al., "Hemostatic Factors and the Risk of Myocardial Infarction or Sudden Death in Patients With Angina Pectoris", The New England Journal of Medicine, Mar. 9, 1995, vol. 332, No. 10, pp. 635-641.
Paul M. Ridker, M.D., et al., "Inflammation, Aspirin, and the Risk of Cardiovascular Disease in Apparently Healthy Men", The New England Journal of Medicine, Apr. 3, 1997, vol. 336, No. 14, pp. 973-979.
JoAnn E. Manson, MD, et al., "A Prospective Study of Aspirin Use and Primary Prevention of Cardiovascular Disease in Women", JAMA, Jul. 24-31, 1991, vol. 266, No. 4, pp. 521-527.
Multiple Risk Factor Intervention Trial Research Group, "Multiple Risk Factor Intervention Trial—Risk Factor Changes and Mortality Results", JAMA, Sep. 24, 1982, vol. 248, No. 12, pp. 1465-1477.
Steering Committee of the Physicians' Health Study Research Group, "Final Report on the Aspirin Component of the Ongoing Physicians' Health Study", The New England Journal of Medicine, Jul. 20, 1989, vol. 321, No. 3, pp. 129-135.
H.B. Berntzen, et al., "Calprotectin (the L1 protein) during surgery in patients with rheumatoid arthritis", Scand J Clin Lab Invest, 1991, pp. 643-650, vol. 51.

* cited by examiner

DETERMINATION METHOD FOR CALPROTECTIN AND THE USE OF CALPROTECTIN AS A PREDICTIVE MARKER FOR CARDIOVASCULAR DISEASE

BACKGROUND OF THE INVENTION

The present invention relates to an assay method for detecting potential for or propensity to cardiovascular disease (CVD) in a subject, e.g. a human or non-human animal, especially a mammal, and in particular to an assay method which may be used to detect a potential for CVD or a propensity to CVD before the onset of CVD symptoms noticeable by the subject.

CVD is a major source of ill health among the human population. In 1998 approximately 40% of all deaths in the western world was a result of CVD (i.e. 1 in every 2.5 deaths). For 2002, it is estimated that, in the USA, over one million people will suffer from a new or recurrent-coronary attack, and more than 40% of the people suffering from these attacks will die. Many of these people will die suddenly without ever having been hospitalised or treated. Many will not have realised that they were susceptible to CVD.

Early or pre-emptive treatment such as a change of diet, reduction or cessation of smoking, increase in exercise, reduction of body weight, etc., has, however, a high success rate of preventing CVD or reducing the propensity to CVD. Thus if CVD or potential for or propensity to CVD can be detected, effective treatment is available.

There is accordingly a need for methods which can be used to detect CVD and especially, the potential for or propensity to CVD, before the disease has progressed beyond the stage where treatment (e.g. change of life style and/or habit) is routinely successful. In particular, there is a need for methods which can be used to detect CVD at the early stages when the symptoms are not apparent to a subject or to a third party, e.g. a physician, i.e. methods for testing "symptom-free" subjects are required.

Such methods may be used to screen the general population (i.e. in mass screening) or at-risk groups within the population, e.g. males over 40, workers in high stress jobs, individuals with unhealthy diets, individuals suffering from clinical obesity, smokers, etc. In cases where potential for CVD or propensity to CVD is diagnosed, pre-emptive treatment may be given and/or the patient may be encouraged to make adjustments to lifestyle and habit.

Likewise, where potential for CVD or propensity to CVD is detected, a patient may be submitted to further testing, e.g. using more expensive or time consuming techniques, such as ECG, with and without physical activity, radioisotope imaging of myocardial perfusion, X-ray (e.g. CT) myocardial angiography, MR myocardial angiography or perfusion imaging, etc. Thus by confirming the possible presence of, or potential for, or propensity to, CVD by using the cheap and facile assay method of the invention in an initial screen (e.g. in a mass screen of "symptom-free" healthy subjects) the likelihood of detecting or identifying undiscovered CVD, or potential for CVD, before health damage becomes irreversible is increased whilst, at the same time, unnecessary use of expensive and time-consuming tests is limited.

By "CVD" is meant any condition of the heart, arteries, or veins which disrupts the supply of oxygen to life-sustaining areas of the body such as the brain, the heart etc. Examples of CVDs are arteriosclerosis, acute myocardial infarction, angina pectoris, ischemic heart disease, cerebrovascular disease, stroke, subarachnoid haemorrhage, intra-cerebral haemorrhage, cerebral infarction, congestive heart failure, angina, heart attack, cardiac arrest and arrhythmia.

The present invention is based on the surprising finding that the protein calprotectin is a useful "marker" or "indicator" of potential for CVD or propensity to CVD before the onset of CVD symptoms (i.e. in symptom-free subjects). In particular it has been surprisingly found that abnormally high calprotectin levels in various body fluids is indicative of susceptibility to CVD before the onset of CVD symptoms is apparent to a subject or to a third party (e.g. a physician).

For the avoidance of doubt, the term calprotectin is used herein synonymously with "L1 protein", "MRP 8/14", "cystic fibrosis (associated) antigen (CFA)" and "calgranulin".

Calprotectin exists in both dimeric and trimeric forms. As a dimer, calprotectin comprises the polypeptide chains S100A8 and S100A9. As a trimer, calprotectin is a 36 kDa heterotrimeric protein with two heavy (14 kD) and one light chain (8 kD) non-covalently linked.

Calprotectin is a calcium binding protein and when bound to calcium, calprotectin is resistant to heat and to proteolysis. This may allow for a wide range of assay techniques and conditions to be employed.

Epitope mapping of calprotectin shows that antibodies with specificity for the complex and/or its single protein chains may be produced. At least four separate immunogenic sites have been shown to exist on the calprotectin complex. Some antibodies recognise either the heavy or the light chain, whilst others recognise both.

Calprotectin is found in cells, tissues and fluids in all parts of the human body and is derived predominantly from neutrophils and monocytes. Calprotectin is probably present in all individuals since amongst more than 5,000 individuals tested, no calprotectin free individual was found. Calprotectin is also found in rats, mice, rabbits, sheep, cattle and pigs. It is therefore an abundant ubiquitous molecule.

In vivo, calprotectin is involved in numerous biological functions including intracellular signal transduction, neutrophil activation, inhibition of intracellular enzymes involved in cell proliferation, antimicrobial activity and in neutrophil defence. Calprotectin is also a regulatory protein in inflammatory reactions and in this role may function to stimulate immunoglobulin production, chemotactic factor activity and neutrophil immobilising factor.

Whilst body fluids probably always comprise calprotectin, the concentration of calprotectin in various body fluids has been found to change, for example, to increase, in a number of disease conditions (e.g. inflammatory, infectious and malignant diseases). Thus measurement of the concentration of calprotectin in body fluid from patients suffering from such disease conditions (i.e. in individuals showing symptoms noticeable to the subject and/or to a third party) and comparing the calprotectin concentration determined to that in body fluid from, for example, a healthy (i.e. a non-diseased) subject may be used as a means of diagnosing such diseases.

For example, whilst the symptoms of bacterial and viral infections are very similar and diagnosis from their symptoms alone may be difficult, the concentration of calprotectin in the plasma/serum of the infected subject increases approximately 1 to 2 times with viral infections but around 1 to 18 times with bacterial infections. Thus the subject having noticed the symptoms of infection, can have the concentration of calprotectin in their body fluid measured and their infection diagnosed and treated accordingly.

Other diseases in which calprotectin may be used as a diagnostic test include: rheumatic diseases (e.g. rheumatoid arthritis, juvenile rheumatoid arthritis, systemic lupus erythematosus), Sjøgrens syndrome, intraocular inflammatory conditions, cystic fibrosis, acute and chronic lung disease, lung carcinoma (squamous cells), pulmonary cancers, colorectal cancer, inflammatory bowel disease, gastric cancer, colorectal adenoma or cancer, Chrohn's disease, ulcerative colitis, gastrointestinal mucosal inflammation, urinary stones, alcoholic liver disease, oral inflammatory mucosal disease, CNS inflammatory disease (e.g. multiple sclerosis and acute encephalitis), HIV infection, secondary CNS infections in HIV infected patients, urinary tract infections, cystitis, pyelonephritis, endogenous posterior uveitis, haematological conditions (e.g. leukaemia), febrile conditions (infectious and non-infectious), acute myocardial infarction and apheresis.

The plasma concentration of calprotectin has also been found to increase during open heart surgery (Semb, A. G. et al, Eur. J. Cardio-thorac Surg. (1991) 5:363-367, Saatvedt, K. et al., Scand. J. Thor. Cardiovasc. Surg. (1996) 30: 53-60, Moen, O. et al., Perfusion (1994) 9:109-117). More specifically, Saatvedt et al. report that calprotectin concentration rises after the start of cardiopulmonary bypass and peaks 48 hours post-operatively.

It has now surprisingly been found that the potential for CVD or propensity to CVD in a subject can be assessed by determining the concentration of calprotectin in a calprotectin-containing sample taken from said subject. In other words, it has been found that determination of the concentration of calprotectin in a calprotectin-containing sample taken from a subject can be used to predict, prior to the onset of symptoms which are noticeable to the subject or to a third party (e.g. a physician) whether or how likely the subject is to suffer CVD.

By "potential for" or "propensity to" is meant the likelihood or probability that the currently symptom-free subject being tested will suffer CVD in the future. This might take the form of an index, ratio, percentage or similar number reflective of the relative risk of CVD in the future (e.g. in the following 1-2 years, at least in the following 6 months).

BRIEF SUMMARY OF THE INVENTION

Thus viewed from one aspect the invention provides an assay method for the detection of potential for CVD or propensity to CVD in a human or non-human animal subject, said method comprising assessing the concentration of calprotectin in a calprotectin-containing sample taken from said subject, e.g. a sample of blood, plasma, serum, cerebrospinal fluid, oral fluid, urine, faeces, synovial or empyema fluid.

DETAILED DESCRIPTION OF THE INVENTION

By "assessing" it is meant that a quantitative or semi-quantitative value for the concentration of calprotectin is determined. This may be the value for the concentration of the sample as tested, e.g. after treatment to remove the cells or other sample components not being assayed for, or to concentrate or dilute the sample or to transfer the calprotectin to a separate medium, e.g. solid substrate.

Alternatively, the assessment may simply be qualitative, i.e. to indicate whether the calprotectin is above or below one or more pre-selected threshold values, e.g. values indicative of absence of potential for CVD or propensity to CVD as detectable by the assay. The precise values for these threshold values or other reference values for calprotectin may depend on the nature of the sample, the age, weight, sex and species of a subject and may be determined in a routine manner by measuring the calprotectin concentration of the relevant body fluid of equivalent subjects without CVD or with CVD at various stages of development.

A value indicative of calprotectin concentration determined or "assessed" in accordance with the method of the invention may be an absolute concentration of calprotectin or may alternatively be an index, ratio, percentage or similar number reflective of the concentration of calprotectin.

A body sample used in the assay method of the invention may be any calprotectin-containing sample, e.g. a body fluid or tissue sample, or a suspension etc. Preferably, the sample will be a body fluid, e.g. urine, cerebrospinal fluid, oral fluid, synovial fluid or empyema fluid, or more preferably, blood or a blood derived sample. When this is the case (i.e. when blood or a blood derived sample is used), the sample used for analysis will preferably be cell-free (e.g. serum or plasma). Alternatively faeces may be used.

The sample may be treated prior to being used in the assay method of the invention. Thus the sample may be treated to remove any cells and/or any sample components not being assayed for. The sample may also be treated to concentrate or dilute the sample or to transfer the calprotectin to a separate medium, e.g. solid substrate. For example the sample may be diluted by adding a buffer or other aqueous medium. Alternatively, a sample, particularly a plasma or serum sample, may be used directly.

The sample is optionally treated with calcium or a calcium mimic (e.g. ions of another alkaline earth metal), prior to being used in the assay method of the invention. The calcium or calcium mimic may be any form which provides $Ca^{2+}$ ions (e.g. $CaCl_2$). If calcium is used then preferably sufficient calcium or calcium mimic is added to the sample to saturate the calcium binding sites of calprotectin. For example, a ten molar excess of calcium source may be added, more preferably, a five molar excess or especially preferably a three molar excess.

While assays for calprotectin are known and may be used in the method of the invention, there has not previously been any suggestion that calprotectin is a marker or indicator of potential for CVD or propensity to CVD. In other words, there has not previously been any suggestion that the calprotectin concentration of symptom-free subjects might be used as a marker or indicator of potential for or propensity to CVD and, in particular, there has not been any suggestion that calprotectin concentration might be used as the marker or indicator in an assay method suitable for mass screening of healthy (i.e. symptom-free) subjects.

Any known assay method for calprotectin may be used in the assay method of the invention. Thus, for example, the method disclosed in U.S. Pat. No. 4,833,074 (Fagerhol et al.) for the isolation of calprotectin and for the subsequent production of monospecific anti-sera thereto may be used to produce anti-calprotectin antibodies for use in any conventional assay method. The anti-calprotectin antibodies produced may be used, for instance, in enzyme linked- and radio- immunoassays.

A NycoCard® (Axis-Shield PoC, Oslo, Norway) immunoassay format for calprotectin may also, for example, be used. This assay uses a solid phase, sandwich-format in which the test device comprises a membrane coated with immobilised anti-calprotectin antibodies. Thus the sample (optionally diluted) is applied to the device and when the sample flows through the membrane, any calprotectin present is captured. The calprotectin immobilised on the membrane is then treated with a gold-antibody conjugate which binds to the calprotectin-antibody complex and the intensity of colour (due to the gold beads), as determined by absorbance of red light, is proportional to the amount of calprotectin. The concentration of calprotectin can therefore be calculated from a calibration curve prepared in the conventional manner.

Alternatively, the commercial test (Calprest®) for calprotectin, for example, in faeces (available from Eurospital®) may be used. This assay uses a polyclonal antibody against calprotectin in an enzyme linked immuno-sorbent assay system. Thus calprotectin present in a sample taken from a subject becomes bound to antibody, which is adsorbed to the surface of a plastic well. A substrate for the enzyme is then added and the intensity of the coloured product produced is proportional to the amount of enzyme and therefore to the amount of calprotectin. The concentration of calprotectin can therefore be calculated from a calibration curve prepared in the conventional manner.

Indeed, both mono- and polyclonal anti-calprotectin antibodies are available commercially. Egg and rabbit polyclonals are, for example, available from Norwegian Antibodies AS and Axis-Shield Diagnostics respectively, whilst mouse monoclonal antibody may be obtained from Dako A/S, Denmark. Any anti-calprotectin antibody obtained, for example, by any conventional technique for making antibodies, may be used in the method of the invention. For instance, rabbit anticalprotectin antibody as well as monoclonal antibodies can be produced according to the protocol described in Harlow and Lane (1988), Antibodies, A Laboratory Manual, Cold Spring Harbor Laboratory, New York, N.Y.

Alternatively, anti-calprotectin antibodies may be prepared by regularly injecting a calprotectin-containing solution into chickens, and then collecting the yolks of the chicken's eggs. Chicken egg polyclonal antibody can then be isolated according to conventional techniques and purified by affinity chromatography.

Preferably, the assay method of the invention is used for mass screening of healthy (e.g. CVD symptom-free) subjects. Where potential for CVD or propensity to CVD is detected, the subject may be subjected to further testing (e.g. using more expensive techniques specific to CVD) to confirm the presence or absence of CVD.

In general, besides the sample under evaluation, calibration samples with known calprotectin content will also be assessed in the performance of the assay method. Such determinations can be used to plot a calibration curve from which the calprotectin content of the sample under investigation may be determined. The nature of the calibration samples and selection of conversion or adjustment factors used in the determination of the calprotectin may vary depending, for example, on the manner in which the calprotectin is detected in the assay technique actually used and on other aspects of the method which affect the assay result, for example, buffer composition, assay conditions etc.

Typically calibration samples having calprotectin contents of 0 to 5000 mg/L will be used. The reference range within which the value for calprotectin concentration will generally be found is 0.1 to 10 mg/L.

In general, the concentration of calprotectin in the serum and plasma of humans with little or no potential for CVD or propensity to CVD will be in the range 0.01-0.75 mg/L. More specifically, the concentration of calprotectin in the serum and plasma of such humans will be in the range 0.05-0.70 mg/L, even more specifically 0.10-0.66 mg/L, for instance, in the range 0.15-0.45 mg/L. For example, the concentration of calprotectin in the serum or plasma of a female with little or no potential for CVD or propensity to CVD will be in the range 0.09-0.53 mg/L, for example, about 0.31 mg/L or 0.30 mg/L. The concentration of calprotectin in the serum or plasma of a male with little or no potential for CVD or propensity to CVD will be in the range 0.12-0.66 mg/L, for example, 0.30-0.39 mg/L, especially 0.31 mg/L.

A calprotectin concentration in serum or plasma of greater than 0.75 mg/L will generally be very strongly indicative of potential for CVD or propensity to CVD. Thus a threshold value above which the assay may be held to be predictive of CVD potential or propensity to CVD may generally be in the range 0.32-0.77 mg/L, for example, about 0.67 mg/L, preferably about 0.70 mg/L, especially about 0.76 mg/L. More preferably the threshold value above which the assay may be held to be predictive of potential for or propensity to CVD is in the range, 0.30-0.50 mg/L, even more preferably in the range 0.32-0.47 mg/L, for example about 0.45 mg/L.

In general, the concentration of calprotectin in the faeces of humans with little or no potential for CVD or propensity to CVD will be in the range 0.01-10 mg/L. More specifically, the concentration of calprotectin in the faeces of such humans will be in the range 0.05-9.0 mg/L, even more specifically 0.50-8.0 mg/L.

A calprotectin concentration in faeces of greater than 10 mg/L will generally be strongly indicative of potential for CVD or propensity to CVD. Thus a threshold value above which the assay may be held to be predictive of CVD potential or propensity to CVD may generally be about 9 mg/L, more preferably about 10.5 mg/L, especially about 11 mg/L.

However, the threshold values are better calculated from calprotectin determinations using the same assay techniques for the same body fluid sample type from a range of patients of similar type (age, sex, weight, species etc.) from healthy through early stage CVD to serious CVD. Even more preferably, the threshold values will be values determined for the same patient at an earlier, healthy stage. Thus, particularly at-risk, individuals could monitor their calprotectin levels on a routine basis (e.g. every 6-months to 1 year) in mass screening programmes.

In a preferred assay method of the present invention, said method further comprises additionally assessing the concentration of another marker for potential to CVD in the sample taken from the subject. Examples of suitable markers may be homocysteine, activated factor XII, cholesterol, cholesterol: HDL ratio, fibrinogen, tissue-type plasminogen activator, Factors V, VII and VIII, lipoprotein (a), von Willebrand factor antigen, plasmin-α2 antiplasmin complex, prothrombin fragment 1+2, thrombin-antithrombin III complex, fibrinopeptide A, fibrin degradation products, D-dimer, activated protein C-resistance, factor VIIc and VIIa, thrombin, serum amyloid A, vascular adhesion molecules and coronary calcium. Preferably the second marker is selected from homocysteine or C-reactive protein.

More preferably the assay method of the present invention further comprises additionally assessing the concentration of C-reactive protein (CRP) in the sample taken from the, subject. Preferably, the concentration of CRP is assessed simultaneously or sequentially to said calprotectin assay.

The measurement of CRP may be effected using any standard immunoassay technique (e.g. ELISA, RIA etc.) or may be determined by NycoCard® (available from Axis-Shield PoC, Oslo, Norway).

A calprotectin concentration in serum or plasma of greater than 0.75 mg/L in addition to a CRP concentration of greater than 1.75 mg/L will generally be very strongly indicative of potential for CVD or propensity to CVD. Preferably, the presence of the above-mentioned concentrations is more strongly indicative of potential for CVD or propensity to CVD than a calprotectin or CRP concentration alone.

Thus threshold values of calprotectin and CRP above which the assay may be held to be highly predictive of CVD potential or propensity,to CVD may generally be 0.32-0.77 mg/L and 1.70 mg/L respectively, more preferably about 0.67 mg/L and 1.75 mg/L respectively, still more preferably about 0.70 mg/L and 2.00 mg/L respectively, especially about 0.76 mg/L and 2.25 mg/L respectively. More preferably the threshold values above which the assay may be held to be predictive of potential for or propensity to CVD are in the range, 0.30-0.50 mg/L and 0.75 mg/L respectively, even more preferably in the range 0.32-0.47 mg/L and 0.75 mg/L respectively, for example about 0.45 mg/L and 0.75 mg/L respectively.

Viewed from a further aspect, the present invention provides an assay kit for use in the method of the invention, said kit comprising reagents and instructions for the performance of the assay method and for the interpretation of the results and, optionally, calprotectin-containing reference samples, and optionally, a detector. Preferably, said assay kit further comprises the reagents and instructions for determination of CRP concentration.

The instructions in the kit may for example be in the form of a label, a manual or an instruction leaflet; however, they may instead take the form of a computer program or a data carrier, e.g. a computer disk.

The detector, where present, will generally be one capable of detecting a reporter species, e.g. a spectrometer, a nuclear radiation detector, a scattered light detector, etc.

The reagents will be agents suitable for calprotectin determination, e.g. suitable reagents are specified in the literature associated with the available tests for calprotectin such as from Eurospital® and NycoCard (available from Axis Shield ASA, Oslo, Norway) cited herein. The reagents mentioned in U.S. Pat. No. 4,833,074 may also be suitable.

A particularly preferred assay method for assessing the concentration of calprotectin in the present invention is a particle-based immunoassay. This is a sensitive technique which is based on turbidimetric determination of the calprotectin concentration. The sensitivity provided by the assay advantageously allows for the relatively low concentrations of calprotectin in body fluid (e.g. plasma or serum) samples to be determined with a high level of precision. At the same time, relatively high concentrations of calprotectin can also be measured with accuracy.

Turbidimetric determination also has the advantage that no solid surface is required for physical separation in the assay and numerous washing and/or separation steps are not required. Thus compared to prior art techniques (e.g. ELISA), the homogenous turbidmimetric determination of calprotectin is quick and easy to perform and may, for instance, be automated. Compared to automation of non-homogeneous techniques involving, for example a solid surface, automation of a turbidimetric based assay is relatively facile. Also, the resulting automated homogenous process is often more reliable being less prone, for example, to break down.

An automated turbidimetric assay is also fast, allowing for a high throughput of samples, and is relatively cheap to run. Typically it can be performed using a commercially available robot, e.g. the Cobas Mira or Hitachi 711, both of which are available from Roche Diagnostics. Such an automated assay is particularly attractive when routine testing of individuals for potential for or propensity to CVD is envisaged.

For turbidimetric determination of calprotectin concentration, the calprotectin-containing sample will generally be a body fluid, e.g. urine, cerebrospinal fluid, oral fluid, synovial fluid or empyema fluid, or more preferably, blood or a blood derived sample. When this is the case, the sample used for analysis will preferably be cell-free (e.g. serum or plasma)

Thus the sample may be treated to remove any cells and/or any sample components not being assayed for. The sample may also be treated to concentrate or dilute the sample or to transfer the calprotectin to a separate medium, e.g. solid substrate. For instance, the sample may be diluted by adding water, a buffer or other aqueous medium. Alternatively, a sample, particularly a serum or plasma sample, may be used directly.

The sample is optionally treated with calcium or a calcium mimic, prior to being used in the assay method. The calcium or calcium mimic may be any form which provides $Ca^{2+}$ ions (e.g. $CaCl_2$). If calcium is used then preferably, sufficient calcium or calcium mimic is added to the sample to saturate the calcium binding sites of calprotectin. For example, a ten molar excess of calcium source may be added, more preferably, a five molar excess or especially preferably a three molar excess.

Opacity, for turbidimetric determination of calprotectin concentration, will generally be generated by contacting the calprotectin-containing sample, or an aliquot thereof, with an anti-calprotectin antibody, antibody fragment or mixture of anti-calprotectin antibodies (e.g. a mixture of monoclonal antibodies). The egg polyclonal anti-human calprotectin antibody commercially available from Norwegian Antibodies AS may, for example, be used to generate opacity. Any anti-calprotectin antibody obtained, for example, by any conventional technique for making antibodies, may be used in the method of the invention.

The antibodies, or antibody fragments, which are used for turbidimetric determination of calprotectin concentration preferably show no or little cross reactions with other blood proteins that may be present in the eluate. The quantity of antibody, or antibody fragment, used should of course be optimised against calprotectin-containing standard samples as opacification arises from the hook effect whereby multiple calprotectin binding generates the opacification centres. Calprotectin, as mentioned above has numerous antibody binding sites, and is particularly suitable for detection in such an assay.

In one preferred embodiment, the anti-calprotectin antibody, or antibody fragment, may be immobilised by binding or coupling, either directly or indirectly, to any well known solid support or matrix which is commonly used for immobilisation. Preferably the solid support or matrix takes the form of particles, preferably nanoparticles. Conveniently the solid support may be made of glass, silica, latex, metal (e.g. gold) or a polymeric material (e.g. polyethylene). Preferably the solid support is made of a polymeric material such as polyethylene.

Binding or immobilisation of the anti-calprotectin antibody or antibody fragment may be achieved using any conventional technique. For example, avidin (available from Pierce Chemical Company) may be immobilised on chloromethyl activated polystyrene nanoparticles (available from Interfacial Dynamic Corporation, US) by agitation in buffer (e.g. at room temperature for 24 hours) and then used in conjunction with biotin labelled anti-calprotectin antibodies (prepared according to conventional techniques in the art). Thus, for example, plasma taken from the subject to be tested for potential for, or propensity to, CVD is added to a solution of avidin-coated nanoparticles in a quartz cuvette of a spectrophotometer, followed by the addition of biotin labelled anti-calprotectin antibody. Turbidimetric readings are then taken.

Alternatively, the biotin labelled antibodies may be added prior to the addition of plasma or serum. In other words, whilst the same reagents are typically used regardless of the instrument used for turbidity detection, the precise sequence in which the various reagents are added may vary. Generally, the sequence used should be in accordance with the instructions accompanying the spectrophotometer used (e.g. a Shimadzu UV-160 spectrophotometer).

Turbidimetric readings are made (i.e. the light absorption at a suitable wavelength is measured at regular intervals) and the light absorption relative to a reference is determined. Optionally, multiple wavelength instruments may be used to make turbidimetric readings and may provide more precise results. Suitable instruments for taking turbidimetric readings include the Cobas Mira, Roche Integra and Merck's Turbiquant.

In an alternative experimental set-up, the anti-calprotectin antibody, or antibody fragment, may be immobilised directly on chloromethyl activated nanoparticles (available from Interfacial Dynamic Corporation, US). For instance, anti-calprotectin antibody (e.g. the egg polyclonal antibody available from Norwegian Antibodies AS) may be mixed with the above-mentioned activated particles in a buffer (10 mM borate, 15 mM sodium chloride, pH 9.0) and agitated (e.g. at room temperature for 24 hours) to furnish anti-calprotectin antibody-coated nanoparticles. Such nanoparticles may be used for turbidimetric determination of calprotectin concentration by adding them to a sample of plasma or serum, taken from the subject to be tested for potential for, or propensity to CVD, in a buffer and taking turbidimetric readings in kinetic mode.

Alternatively, the plasma or serum may be added to the anti-calprotectin antibody-coated nanoparticles. In other words, whilst the same reagents are typically used regardless of the instrument used for turbidity detection, the precise sequence in which the various reagents are added may vary. Generally, the sequence used should be in accordance with the instructions accompanying the spectrophotometer used (e.g. a Shimadzu UV-160 spectrophotometer).

Examples of automated robots which are suitable for taking turbidimetric readings in accordance with the assay method of the invention include the Cobas Mira and Hitachi 711, both of which are available from Roche Diagnostics.

The particles to which the antibody, or antibody fragment, may be bound are typically spherical. The size of the particles used in the assay may effect the precision with which the calprotectin concentration is measured. Whilst larger particles allow for lower concentrations of calprotectin to be detected, their reduced surface area means that they have a lower binding capacity. For example, doubling the particle diameter, halves the binding capacity of a mass unit of particles.

Additionally increasing the particle diameter increases the level of background light absorbance and light suspension at the wavelengths typically used in such assays (e.g. 330 to 600 nm). Thus whilst larger particles increase the sensitivity of the assay, this may be accompanied by some loss of accuracy and in particular, an increase in the number of false negative results obtained. This is particularly likely to be the case with samples containing relatively high calprotectin concentrations (i.e. those samples obtained from individuals with a high potential for or propensity to CVD) wherein the nanoparticle-bound binding sites may become saturated without all of the calprotectin becoming bound.

These counter-acting effects associated with changing the particle size (e.g. increasing the particle size increases sensitivity but decreases accuracy) represents a significant problem to be overcome in the development of a sensitive assay for detecting the range of levels of calprotectin present in body fluids.

Also it is preferable in the assay method of the invention that the particles used allow for a wide range of calprotectin concentrations to be determined with precision. This may mean that a high level of confidence can be attributed to both a negative result (i.e. a concentration falling below the threshold value) as well as a positive result. It is particularly preferred in the assay method of the invention that samples having a calprotectin concentration in the range 0.5-50 mg/L (e.g. 1-40 mg/L) can be measured.

The particles to which the antibody, or antibody fragment, may be bound are typically spherical with a diameter of 1-150 nm, for example 10-90 nm or 15-60 nm, for instance, 44 nm. In a particularly preferred assay method of the invention the particles to which the antibody or antibody fragments are bound have a diameter of 55-140 nm, more preferably 65-110 nm, for example, 70-90 nm.

Alternatively the diameter of the particles can be measured once antibodies or antibody fragments are bound to their surface. In this case, the diameter of the antibody or antibody fragment coated particles is preferably 65-140 nm, more preferably 75-120 nm, still more preferably 80-100 nm. Coated particles of these sizes are especially preferred when the sample tested is plasma.

The particles, in both the "nude" and coated states, preferably have a diameter which does not itself enable absorption of the wavelength of light used for spectrophotometric determination. Thus the suspension of coated nanoparticles is approximately (e.g. substantially) transparent until calprotectin induced aggregate formation occurs resulting in the formation of aggregates having a larger diameter. Such aggregates have the ability to absorb the wavelength of light used by the spectrophotometer.

Further, the particles are preferably substantially all of the same size, more specifically all of the same diameter. Preferably, monodisperse metal (e.g. gold) or polymer particles are used. Monodisperse polymer particles are available from Dynal Biotech AS, Oslo, Norway.

Whilst not wishing to be bound by theory, it may be that the use of immobilised antibody or antibody fragments increases the sensitivity of the assay by increasing the size of any calprotectin derived opacity generating sites and therefore the amount of light scattered therefrom. By using a solid support or matrix (e.g. nanoparticles) which is substantially all of the same size it may be that the sensitivity of the turbidimetry assay is further increased.

As is routine in turbidimetric assays, a polymeric opacification enhancer, such as polyethyleneglycol, is preferably also added to the eluate.

Before the turbidimetric determination is made, the fraction, antibody or antibody fragment, preferably bound to a nanoparticle, and optionally enhancer may be incubated for a short period, e.g. 5 minutes to an hour, preferably about 10 minutes, at room temperature. Optionally, in determining calprotectin concentration using the turbidimetry technique, a kinetic reading mode may be used.

The light used in the determination of opacification should have an appropriate wavelength, for example, 300-600 nm. In this regard it was found that use of a 300-450 nm filter, preferably a 340 nm or a 405 nm filter, furnished particularly good results. Use of a 560 nm filter may also yield especially good results.

In general, in addition to the sample under evaluation calibration samples with known calprotectin contents will also be assessed in the performance of the assay method. Such determinations can be used to plot a calibration curve from which the calprotectin content of the sample under evaluation can be determined. Preferably calibration samples having calprotectin contents of up to 5000 mg/L (e.g. 1500, 1000, 750, 250, 100) or up to 100 mg/L (e.g. 75, 50, 25, 5, 1.0 and 0.5 mg/L) will be used. More preferably the calibration samples have a calprotectin content of up to 10 mg/L (e.g. 10, 8, 6, 4, 2 mg/L), still more preferably up to 5 mg/L (5, 4.5, 4, 3.5, 3, 2.5, 2, 1.5, 1, 0.5 mg/L).

The above described turbidimetric assay for the determination of calprotectin is surprisingly reliable, quick, cheap, facile and amenable to automation. This is in contrast to the currently available assay methods which are relatively complex and are not directly applicable to the automated multi-task diagnostic machines commonly used by diagnostic laboratories.

Automation is particularly desirable where numerous mixing, addition and/or dilution steps are involved since these may be achieved with a higher degree of accuracy. Robots may also offer a higher level of reliability and/or reproducability. Automation also increases throughput.

The currently available assay methods which may offer reasonable levels of precision (e.g. ELISA) are, however, difficult to automate. This is at least in part because they typically involve numerous washing and separation steps (e.g. attachment to a solid surface) and automation of non-homogeneous processes is often problematic. Also these processes typically involve a relatively large number of steps which increases the complexity of any automated protocol. Other conventional techniques for determination of calprotectin (e.g. nephelometry) offer high precision but require special equipment to carry out the necessary measurements. Specialised equipment is not typically easy to incorporate into an automated protocol.

Indeed there is a continuing need for cheap, reliable, quick and facile calprotectin assays for use in diagnostic techniques.

Thus, according to a further aspect, the present invention provides an assay method for the determination of calprotectin in a calprotectin-containing body fluid, said method comprising the steps of:

(a) obtaining a calprotectin-containing liquid sample of, or derived from, said fluid;

(b) contacting said sample of said body fluid with an, optionally nanoparticle-bound, anti-calprotectin antibody or antibody fragment, to bind said calprotectin;

(c) optionally, adding an opacity enhancer; and (d) assessing the calprotectin content by turbidimetry.

Such as assay may be useful in the diagnosis of various disease conditions which are characterised by abnormal levels (e.g. high levels) of calprotectin. Such disease conditions include: rheumatic diseases (e.g. rheumatoid arthritis, juvenile rheumatoid arthritis, systemic lupus erythematosus), Sjøgrens syndrome, intraocular inflammatory conditions, cystic fibrosis, acute and chronic lung disease, lung carcinoma (squamous cells), pulmonary cancers, colorectal cancer, inflammatory bowel disease, gastric cancer, colorectal adenoma or cancer, Chrohn's disease, ulcerative colitis, gastrointestinal mucosal inflammation, urinary stones, alcoholic liver disease, oral inflammatory mucosal disease, CNS inflammatory disease (e.g. multiple sclerosis and acute encephalitis), HIV infection, secondary CNS infections in HIV infected patients, urinary tract infections, cystitis, pyelonephritis, endogenous posterior uveitis, haematological conditions (e.g. leukaemia), febrile conditions (infectious and non-infectious), acute myocardial infarction and apheresis.

Thus viewed from a further aspect the invention provides a method of diagnosis of any of the above-mentioned diseases, comprising the method as described hereinbefore followed by comparison of said calprotectin content with a predetermined threshold value. The threshold value indicative of any particular disease state may be determined by any conventional method known in the art. Preferably the method is used for the diagnosis of CVD.

A body sample used in the turbidimetric assay method may be any calprotectin-containing sample, e.g. a body fluid or tissue sample, or a suspension etc. Preferably, the sample will be a body fluid, e.g. urine, cerebrospinal fluid, oral fluid, synovial fluid or empyema fluid, or more preferably, blood or a blood derived sample. When this is the case (i.e. blood or blood derived sample is used), the sample used for analysis will preferably be cell-free (e.g. serum or plasma). Alternatively faeces may be used.

Preferably, the body sample is selected to provide the most sensitive indication of the disease being diagnosed. Thus whilst blood, plasma or serum might be tested to diagnose infections (e.g. HIV, bacterial infection), rheumatic disease, leukaemia etc., faeces might be tested during diagnosis of diseases associated with the gastrointestinal tract (e.g. Crohn's disease, ulcerative colitis, colorectal cancers).

Viewed from yet a further aspect, the invention provides a kit for a diagnostic turbidimetric assay according to the invention, said kit comprising:

preferably, a calprotectin solution of known concentration and more preferably a set of such solutions having a range of calprotectin concentrations;

one or more anti-calprotectin antibodies or antibody fragments, optionally immobilised on a solid support (e.g. nanoparticles);

preferably, a light transmitting vessel;

preferably, an opacification enhancer; and preferably, a detector.

If desired an automated apparatus may be arranged to receive a calprotectin-containing body fluid sample, apply the anti-calprotectin antibody or antibody fragment, optionally immobilised on a solid support (e.g. nanoparticles), optionally apply an opacification enhancer, and assess calprotectin content. Such an apparatus is also deemed to fall within the scope of the invention.

The invention will now be described further with reference to the following non-limiting Examples and the accompanying figures in which:

| Anderson-Darling Normality Test | |
|---|---|
| $A^2$: | 8.160 |
| P-value: | 0.000 |
| Mean | 0.403 |
| Standard Deviation | 0.238 |
| Variance | 0.057 |
| Skewness | 1.679 |

-continued

| Anderson-Darling Normality Test | |
|---|---|
| Kurtosis | 3.302 |
| N | 199 |
| Minimum | 0.070 |
| 1st Quartile | 0.240 |
| Median | 0.340 |
| 3rd Quartile | 0.500 |
| Maximum | 1.370 |
| 95% confidence limit for Mu | 0.370 |
|  | 0.436 |
| 95% confidence limit for Sigma | 0.217 |
|  | 0.264 |
| 95% confidence limit for Median | 0.310 |
|  | 0.370 |

Figure 2:
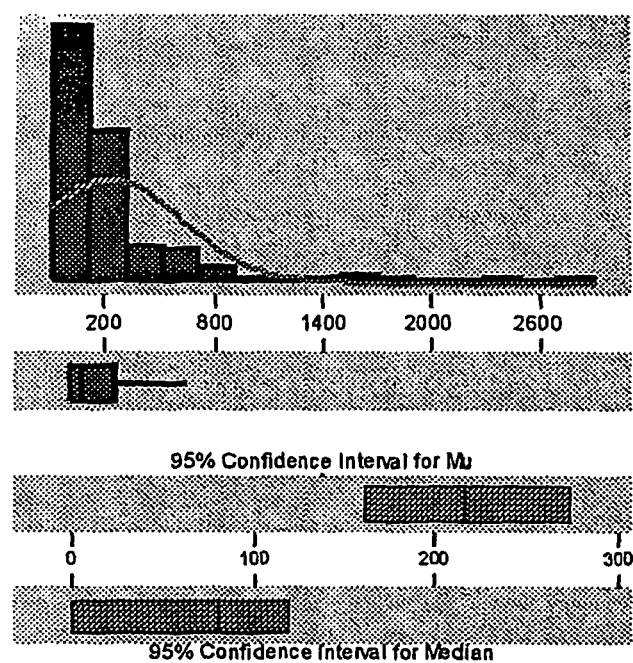

FIG. 2 is the distribution curve for calcium score in the 200 subjects tested. The summary statistics for FIG. 2 are:

| Anderson-Darling Normality Test | |
|---|---|
| $A^2$: | 25.037 |
| P-value: | 0.000 |
| Mean | 217.060 |
| Standard Deviation | 399.000 |
| Variance | 159201 |
| Skewness | 3.462 |
| Kurtosis | 15.341 |
| N | 200 |
| Minimum | 0.00 |
| 1st Quartile | 0.00 |
| Median | 78.00 |
| 3rd Quartile | 259.25 |
| Maximum | 2794.00 |
| 95% confidence limit for Mu | 161.42 |
|  | 272.70 |
| 95% confidence limit for Sigma | 363.35 |
|  | 442.46 |
| 95% confidence limit for Median | 0.00 |
|  | 117.33 |

Figure 3:
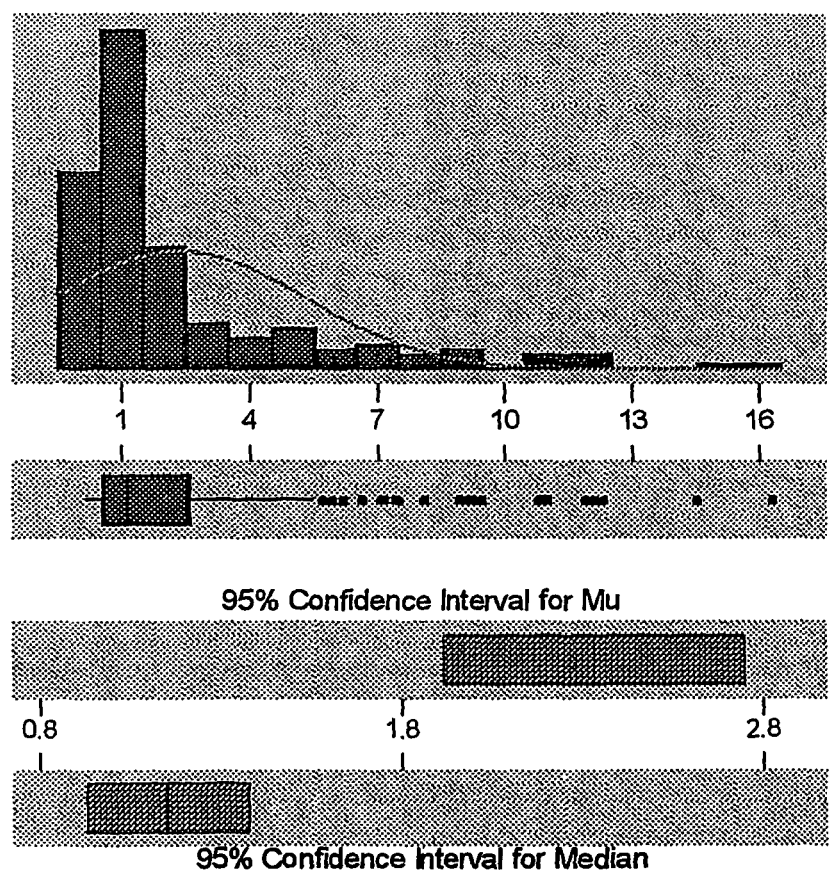

FIG. 3 is the distribution curve for hsCRP in the 200 subjects tested. The summary statistics for FIG. 3 are:

| Anderson-Darling Normality Test | |
|---|---|
| $A^2$: | 21.221 |
| P-value: | 0.000 |
| Mean | 2.331 |
| Standard Deviation | 2.970 |
| Variance | 8.819 |
| Skewness | 2.243 |
| Kurtosis | 5.103 |
| N | 197 |
| Minimum | 0.150 |
| 1st Quartile | 0.540 |
| Median | 1.150 |
| 3rd Quartile | 2.580 |
| Maximum | 16.30 |
| 95% confidence limit for Mu | 1.913 |
|  | 2.748 |
| 95% confidence limit for Sigma | 2.703 |
|  | 3.296 |
| 95% confidence limit for Median | 0.933 |
|  | 1.375 |

Figure 4:
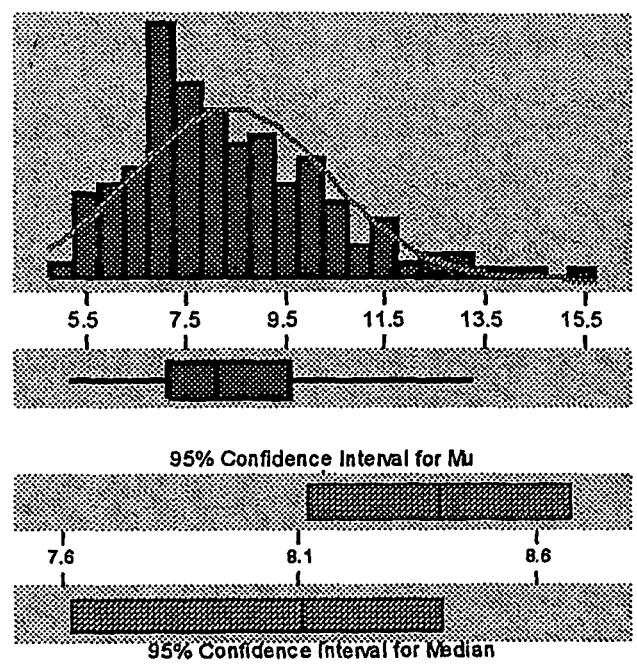

FIG. 4 is the distribution curve for homocysteine in the 200 subjects tested. The summary statistics for FIG. 4 are:

| Anderson-Darling Normality Test | |
|---|---|
| $A^2$: | 2.535 |
| P-value: | 0.000 |
| Mean | 8.391 |
| Standard Deviation | 1.966 |
| Variance | 3.867 |
| Skewness | 0.875 |
| Kurtosis | 0.730 |
| N | 199 |
| Minimum | 5.100 |
| 1st Quartile | 7.100 |
| Median | 8.100 |
| 3rd Quartile | 9.600 |
| Maximum | 15.300 |
| 95% confidence limit for Mu | 8.117 |
|  | 8.666 |
| 95% confidence limit for Sigma | 1.790 |
|  | 2.181 |
| 95% confidence limit for Median | 7.620 |
|  | 8.400 |

Figure 5:
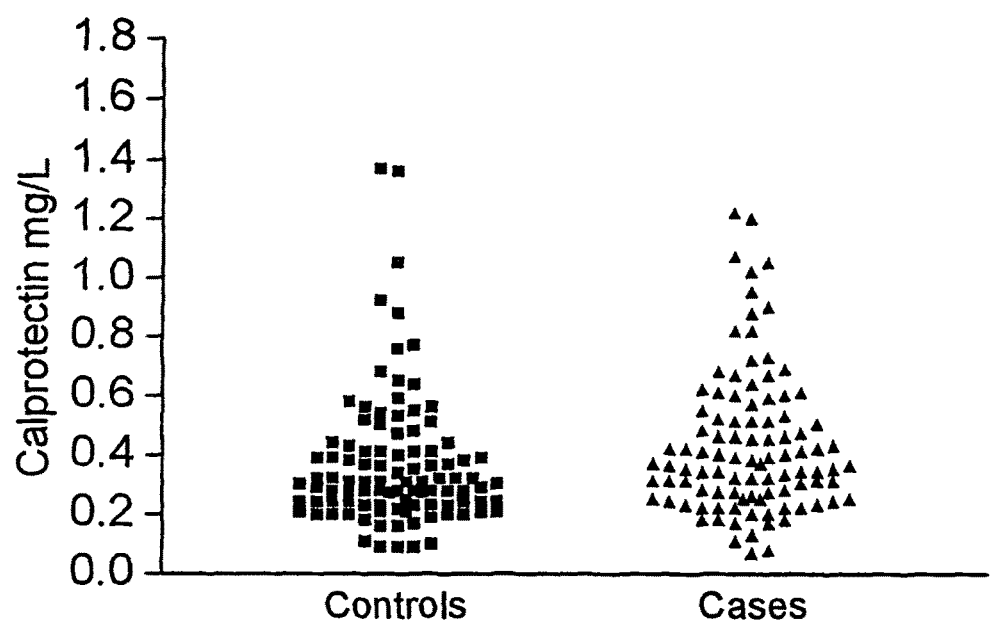
Figure 6:
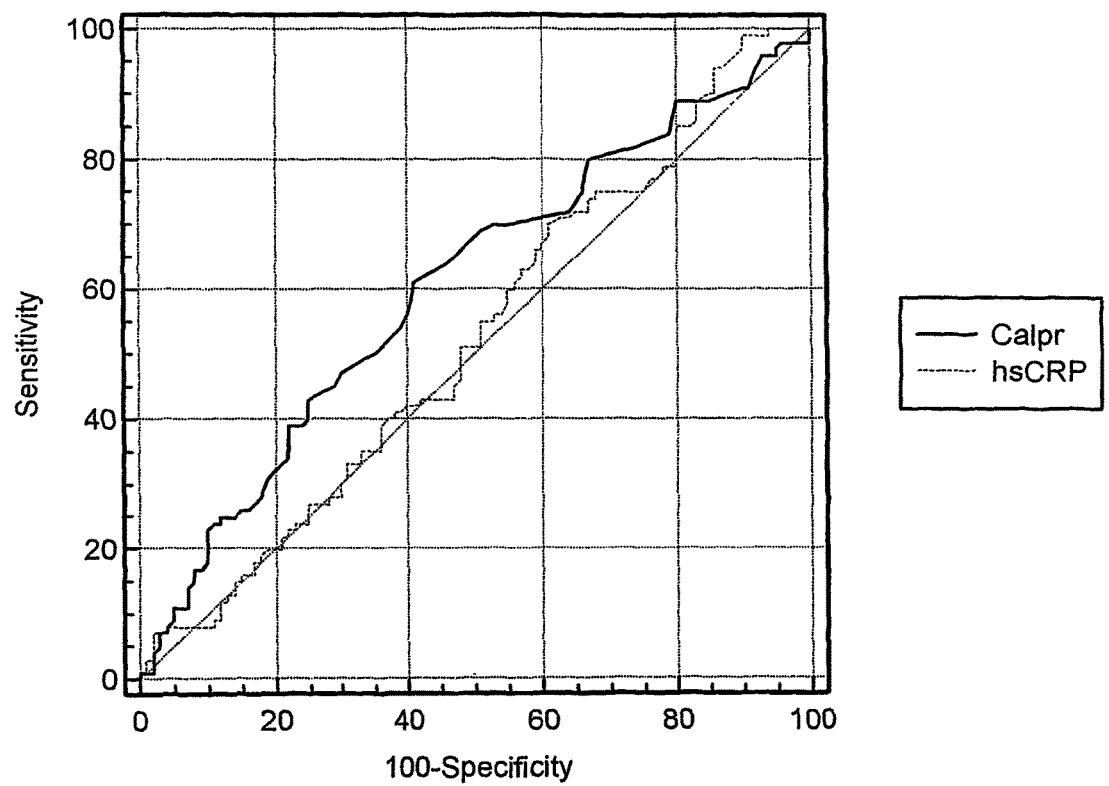
Figure 7:
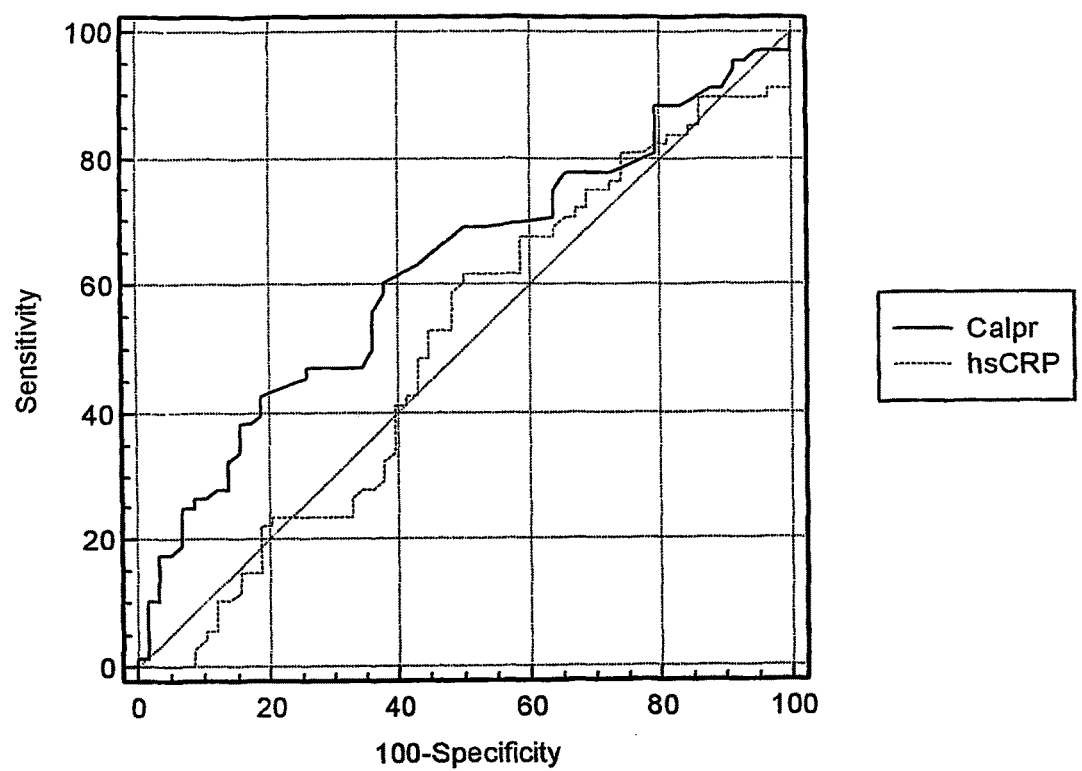

FIG. 5 is a dot plot for the distribution of calprotectin between the calcium positive and calcium negative results; and FIGS. 6 and 7 are the ROC curves for calprotectin and hsCRP for all 200 subjects tested and for the male subjects tested respectively.

EXAMPLE 1

Anti-Calprotectin Antibody (a) Isolation of Calprotectin

Calprotectin may be isolated according to the methods described in Examples 1 and 2 of U.S. Pat. No. 4,833,074 (Fagerhol).

Calprotectin may alternatively be purified from human buffy coats. A cell-suspension in 2.5 mM EDTA is made by the addition of EDTA (50 mM, pH 7) to cells. The cells are then washed in 160 mM ammonium chloride/10 mM sodium hydrogen carbonate for 3 minutes and centrifuged (160×g) for 10 minutes at 4° C. The resulting pellet is washed in EDTA (2.5 mM)/NaCl (150 mM) and centrifuged (55×g) for a further 10 minutes at 4° C. The pellet is then resuspended in 0.625 mM EDTA/18.75 mM Diemal, pH 7.4 and frozen at −70° C. for at least 24 hours.

Following thawing, the resulting material is centrifuged (at 3700×g) for 30 minutes, then the supernatant is removed and filtered (with a 0.45 μm filter available from Millipore), then loaded onto a DEAE (diethylaminoethyl) Sepharose ion-exchange column (available from Pharmacia), pre-prepared using a binding buffer (e.g. 0.63 mM EDTA/18.75 mM Diemal, pH 7.4). Any non-binding material passes through the column and is eluted. Once all of the non-binding material is eluted from the column, pure calprotectin is eluted using a calcium-containing elution buffer (e.g. 75 mM Diemal buffer/10 mM CaCl$_2$). About 25 mg calprotectin is obtained per buffy coat.

(b) Preparation of Anti-Calprotectin Antibody

Anti-calprotectin antibodies may be prepared according to the method described in Example 3 of U.S. Pat. No. 4,833,074 (Fagerhol)

Chicken egg polyclonals may alternatively be prepared. A solution comprising calprotectin (0.5 mg/ml) and Freund's adjuvant is injected into chickens every 14 days four times (or for two months), and then once every 1 month. After 12 weeks, the eggs of the calprotectin-injected chicken may be collected and their yolks removed (without the film). Following dilution in HCl (5 mM), the yolk is centrifuged and the supernatant is collected. The supernatant is then filtered and treated with saturated ammonium sulfate to a final concentration of 3.8 M. The mixture is centrifuged and the precipitate produced is collected and dissolved in buffer (0.11 M sodium acetate, 0.15 M NaCl, pH 7.4). The resulting solution is finally dialysed with a membrane having a pore size of 10,000 kD and then purified by affinity chromatography.

The column typically used for affinity chromatography comprises an activated matrix of succinimide-activated sepharose (HiTrap NHS activated available from Amersham-Pharmacia) which is suitable for the immobilisation of calprotectin. More specifically, the activated resin reacts spontaneously, at pH 7-8, with free amines in the calprotectin. For chromatography the dialysis solution is usually diluted to a concentration of about 3 mg/ml in PBS prior to its application to the column. The anti-calprotectin antibodies are subsequently eluted using 6 M urea in ice cold PBS or 0.1 M sodium citrate solution, pH 3.0. Preferably, 0.1 M sodium citrate solution is used. Following elution, the anti-calprotectin antibody containing fractions are immediately diluted and dialysed in PBS.

EXAMPLE 2

Turbidimetric Assay for Calprotectin (a) Preparation of Avidin-coated Nanoparticles 600 μm of 4.2% w/v chloromethyl activated nanoparticles (diameter 44 nm) available from Interfacial Dynamic Corporation, US are dialysed against water with a membrane having a pore size of 10,000 kD. 0.5 ml of a borate (10 mM) and sodium chloride (15 mM) solution at pH 9.0 is added and mixed. 10 mg avidin, dissolved in 0.5 ml of a 10 mM borate and 15 mM NaCl solution at pH 9 (available from Pierce Chemical Company) is added and the mixture is agitated at room temperature for 24 hours. 40 μl of glycine solution (2M, pH 9.0) is then added and the mixture is agitated for a further 4 hours at room temperature.

The particles are then diluted to a volume of 100 ml and diafiltrated, firstly in 500 ml of a 10 mM borate and 15 mM sodium chloride solution at pH 9.0 and secondly in a 25 mM Tris, 150 mM sodium chloride and 0.01% Tween® 20 solution at pH 7.4 (available from Sigma US) using a Pellicon XL Filter (cut off 300,000) and a labscale TTF System (available from Millipore) in accordance with the instructions supplied from the instruments suppliers. The desired concentration of avidin-coated nanoparticles is finally obtained by centrifugation and re-suspension of the particles in a 25 mM TRIS, 150 mM sodium chloride and 0.01% Tween® 20 solution. Any aggregates formed during this preparation procedure may be removed by slow centrifugation.

(b) Assay for Calprotectin using Avidin-coated Nanoparticles

A suspension having a concentration of about 0.30 mg particles of the above-described avidin-coated nanoparticles per ml is prepared by centrifugation and re-suspension of the above-described preparation in a 25 mM TRIS, 150 mM NaCl, 0.1% Tween® 20 and 2% PEG 6000 solution at pH 7.4 (available from Sigma). 500 μl of this particle suspension is mixed with a plasma sample (about 20 μl), taken from a subject being tested for propensity to CVD, in a reading quartz cuvette of a recording spectrophotometer (e.g. a Shimadzu UV-160). The absorption of 340 nm monochromatic light is recorded and after 60 s, 75 μg of anti-calprotectin antibody labelled with 0.15 nmol biotin (e.g. biotin labelled affinity purified egg polyclonal purchased from Norwegian Antibodies AS, Norway), diluted in 50 μl of a 25 mM TRIS, 150 mM NaCl and 0.1% Tween® 20 solution at pH 7.4 is added to the quartz cuvette and mixed. The absorption of 340 nm monochromatic light is immediately recorded using a reference cuvette containing a solution of 25 mM TRIS, 150 mM NaCl and 0.1% Tween® 20 at pH 7.4, and again at regular intervals (e.g. every 2 minutes) until about 15 minutes has elapsed. The increase in absorption at each time point is calculated in accordance with standard turbidimetric reading in kinetic mode or "end-point" readings. That is, the increase in light absorption at each time-point is calculated relative to the reading made prior to the addition of antibody-coated nanoparticles and/or at the end of the recording.

A calibration curve is constructed by carrying out an identical procedure with standards having a known concentration of calprotectin. The concentration of calprotectin in the sample can then be calculated from the calibration curve.

EXAMPLE 3

Alternative Turbidimetric Assay for Calprotectin (a) Preparation of Anti-Calprotectin Antibody Coated Nanoparticles 1 ml of 4.2% w/v chloromethyl activated nanoparticles (diameter 44 nm) available from Interfacial Dynamic Corporation, US are dialysed against water with a membrane having a pore size of 10,000 kD. 0.5 ml of a 10 mM borate and 15 mM sodium chloride solution at pH 9.0 is then added. 27 mg of purified anti-calprotectin antibodies (e.g. affinity purified egg polyclonal antibodies available from Norwegian Antibodies AS, Norway) are dialysed against a 10 mM borate and 15 mM sodium chloride solution at pH 9.0.

Following addition of the nanoparticles to the purified anti-calprotectin antibodies the mixture is agitated for 24 hours at room temperature. 40 μl of a glycine solution (2 M at pH 9.0) is then added and the mixture is agitated for a further 4 hours at room temperature.

The particles are then diluted to total volume of 100 ml and diafiltrated against 1000 ml of a 10 mM borate and 15 mM sodium chloride solution at pH 9.0 to which 0.1% Tween® 20 and 3 mg/ml egg albumin is added using a Pellicon XL filter (cut of 300,000) and a labscale TFF system (available from Millipore) in accordance with the instructions supplied from the instruments suppliers. The desired concentration of anti-calprotectin antibody-coated nanoparticles is finally obtained by centrifugation and re-suspension of the particles in solution. Any aggregates formed during this preparation procedure may be removed by slow centrifugation.

(b) Assay for Calprotectin using Anti-calprotectin Antibody-coated Nanoparticles A suspension comprising 400 μg of the above-described antibody-coated nanoparticles in 50 μl of a 10 mM borate, 15 mM NaCl, 0.1% Tween® 20, 3 g/l egg albumin solution at pH 9.0 is prepared.

Simultaneously, 20 μl of plasma, taken from the subject being tested for potential for CVD, in 500 μl assay buffer (25 mM TRIS, 150 mM NaCl, 0.1% Tween® 20 and 2% PEG 6000 at pH 7.4 (available from Sigma) is put in a reading quartz cuvette of a recording spectrophotometer (e.g. Shimadzu UV-160) and the light absorption of 340 nm monochromatic light is measured. After 60 s, the above-mentioned suspension comprising 400 μg of antibody-coated nanoparticles is added, and mixed in the cuvette. The light absorption immediately after adding the antibody-coated nanoparticles is recorded, and again at regular intervals (e.g. every 2 minutes) until about 15 minutes has elapsed. The increase in light absorption at each time-point is calculated relative to the reading made prior to the addition of antibody-coated nanoparticles and/or at the end of the recording. In other words, turbidimetric readings in kinetic mode or "end-point" readings are made.

A calibration curve is also constructed by carrying out an identical procedure with standards having a known concentration of calprotectin. The concentration of calprotectin in the sample can then be calculated from the curve.

EXAMPLE 4

Turbidimetric Assay for Calprotectin (a) Preparation of Streptavidin-coated Nanoparticles 600 µm of 4.2% w/v chloromethyl activated nanoparticles (diameter 67 nm) available from Interfacial Dynamic Corporation, US are dialysed against water with a membrane having a pore size of 10,000 kD. 0.5 ml of a phosphate (10 mM) and sodium chloride (150 mM) buffer solution at pH 7.4 is added together with 10 mg streptavidin, dissolved in 0.5 ml of a 10 mM phosphate and 150 mM NaCl buffer solution at pH 7.4 (available from Pierce Chemical Company) and the mixture is agitated at room temperature for 24 hours. 40 µl of glycine solution (2M, pH 9.0) is then added and the mixture is agitated for a further 4 hours at room temperature.

The particles are then diluted to a volume of 100 ml and diafiltrated, firstly in 500 ml of a 10 mM borate and 15 mM sodium chloride solution at pH 9.0 and secondly in a 25 mM Tris, 150 mM sodium chloride and 0.01% Tween® 20 solution at pH 7.4 (available from Sigma US) using a Pellicon XL Filter (cut off 300,000) and a labscale TTF System (available from Millipore) in accordance with the instructions supplied from the instruments suppliers. The desired concentration of avidin-coated nanoparticles is finally obtained by centrifugation and re-suspension of the particles in a 25 mM TRIS, 150 mM sodium chloride and 0.0% Tween® 20 solution. Any aggregates formed during this preparation procedure may be removed by slow centrifugation.

The mean particle size of the streptavidin coated nanoparticles was measured to be 82 nm by Sinteff AS, Norway.
(b) Assay for Calprotectin using Streptavidin-coated Nanoparticles A suspension having a concentration of about 0.60 mg particles of the above-described avidin-coated nanoparticles per ml is prepared by centrifugation and re-suspension of the above-described preparation in a 25 mM TRIS, 150 mM NaCl, 0.1% Tween® 20 and 1% PEG 6000 solution at pH 7.4 (available from Sigma). 500 µl of this particle suspension is mixed with a plasma sample (about 5 µl), taken from a subject being tested for propensity to CVD, in a reading quartz cuvette of a recording spectrophotometer (e.g. a Shimadzu UV-160). The absorption of 560 nm monochromatic light is recorded and after 60 s, 75 µg of anti-calprotectin antibody labelled with 0.15 nmol biotin (e.g. biotin-labelled affinity purified egg polyclonal purchased from Norwegian Antibodies AS, Norway), diluted in 50 µl of a 25 mM TRIS, 150 mM NaCl and 0.1% Tween® 20 solution at pH 7.4 is added to the quartz cuvette and mixed. The absorption of 340 nm monochromatic light is immediately recorded using a reference cuvette containing a solution of 25 mM TRIS, 150 mM NaCl and 0.1% Tween® 20 at pH 7.4, and again at regular intervals (e.g. every 2 minutes) until about 15 minutes has elapsed. The increase in absorption at each time point is calculated in accordance with standard turbidimetric reading in kinetic mode or "end-point" readings. That is, the increase in light absorption at each time-point is calculated relative to the reading made prior to the addition of antibody-coated nanoparticles and/or at the end of the recording.

A calibration curve is constructed by carrying out an identical procedure with standards having a known concentration of calprotectin. The concentration of calprotectin in the sample can then be calculated from the calibration curve.

EXAMPLE 5

(a) Preparation of Anti-Calprotectin Antibody Coated Nanoparticles 1 ml of 4.2% w/v chloromethyl activated nanoparticles (mean diameter 67 nm) available from Interfacial Dynamic Corporation, US, are dialysed against water with a membrane having a pore size of 10.000 kD, and then diluted to 10 ml with water. 27 mg of purified egg polyclonal antibodies ( e.g. affinity purified egg polyclonal antibodies available from Norwegian Antibodies AS, Norway) are dialysed against a 10 mM borate and 15 mM sodium chloride buffer solution and finally diluted to 6 ml in the same 10 mM borate and 15 mM sodium chloride solution at pH=9.0.

Under agitation, the particles are mixed with the antibodies, and agitation is continued at room temperature for 24 hours. 40 µl of a glycine solution (2 M at pH 9.0) is then added and the mixture is agitated for a further 4 hours at room temperature.

The particles are then diluted to a total volume of 100 ml in 10 mM borate, 15 mM sodium chloride buffer to which 0.1% Tween® 20 and 3 mg/ml egg albumin is added and diafiltrated against 1000 ml of said borate/sodium chloride buffer to which 0.1% Tween® 20 and 3 mg/ml egg albumin is added, using a Pellicon XL filter (cut off 300.000 D) and a labscale TFF system (available from Millipore) in accordance with the instructions supplied from the instrument suppliers, and in the end the particles are concentrated to a volume of 40 to 100 ml.

The mean diameter of the particles obtained was measured to be 81 nm by Sinteff AS, Norway.
(b) Assay for Calprotectin using Anti-calprotectin Antibody-coated Nanoparticles A suspension of 0.7 mg/ml of the above described anti-calprotectin antibody coated particles is made in 0.25 mM TRIS, 0.15 M NaCl and 0.1% Tween at pH 8.0.

5 µl of a plasma sample, taken from the subject being tested for CVD, is dissolved in assay buffer (460 µl, 25 mM TRIS, 150 mM NaCl, 0.1% Tween, 1.0% polyethyleneglycol 6000, pH=7.4) in a reading quartz cuvette in a recording spectrophotometer (e.g. Shimadzu UV-160) and the light absorption of 560 nm monochromatic light is measured. After 60 s, 100 µl of the above mentioned suspension comprising 0.7 mg/ml of antibody coated nanoparticles is added, and mixed in the cuvette. The light absorption before and immediately after adding the antibody-coated nanoparticles is recorded, and again at regular intervals (eg. every 20 s) until 15 minutes has elapsed. The increase in light absorption at each time point is calculated relative to the reading made prior to the addition of antibody coated nanoparticles and at the end of the recording. In other words, turbidimetric readings in kinetic mode and/or "end point" readings are made.

A calibration curve is also constructed by carrying out an identical procedure with standards having a known concentrations of calprotectin. The concentration of calprotectin ib the sample can then be calculated from the curve.

EXAMPLE 6

Statistical Analysis

Comparison of Calprotectin and Other Markers for Detection of Potential for CVD or Propensity to CVD Coronary calcification has been shown to be strongly associated with the occurrence of CVD and has also been demonstrated to be a useful method for predicting potential for CVD (e.g. mycocardial infarction or stroke).

The extent of coronary calcification is quantitatively measured used electron-beam computed tomography (EBCT) and is represented by a calcium score (CS). A high calcium score represents a high level of calcification and a high risk of developing CVD.

In the following study the CS of 200 subjects (100 controls having a CS<100 and 100 cases having a CS>100) aged 45 or greater was-tested as well as their calprotectin, CRP and homocysteine plasma or serum levels. The subjects were either self- or physician-referred asymptomatic individuals and had had an EBCT scan within the previous 2 years (usually within the previous 6 months) to testing of their plasma or serum for the concentration of calprotectin, CRP and homocysteine.

Methods
Calprotectin

Calprotectin was measured by the Calprest® test (distributed by Eurospital®, Italy) and data were summarised for the patient and the control group using standard deviation, median, minimum and maximum. 95% confidence intervals for median were calculated. The Anderson-Darling calculation was used as a test for normality.

Calprotectin was also summarised by gender using the same summary statistics.

Calcium Score (CS)

Calcium score was determined by Electron-Beam Computed Tomography (EBCT) scanning. Data for case and control groups were summarised.

High Sensitive C-Reactive Protein (hsCRP)

hsCRP was determined by Dade Behring's "N High Sensitivity CRP" assay (Roberts et al., Clinical Chemistry, 2000, 46:4, p 461-468). Data were summarised for the patient and the control groups using mean, standard deviation, median, minimum and maximum.

Homocysteine (Hyc)

Plasma Homocysteine (Hcy) was determined by the Abbott IMx method (Shipchandler, M. T. and Moore E. G., Clinical Chemistry, 1995, 41:7, p. 991-994). Data were summarised for the patient and the control groups using standard deviation, median, minimum and maximum.

Comparison between CS and Calprotectin, hsCRP, Hcy
(i) Chi-squared

The Chi-squared test was used to test for covariance between pairs of markers.
(ii) Odds Ratio The odds ratio used with the 2×2 cross-tabulation (i.e the chi-squared table) is the ratio of the odds of two tests co-varying to the odds of two tests disagreeing. Therefore, the odds ratio may be interpreted as a measure of the magnitude of association between the two tests.

Odds ratio was calculated for CS versus calprotectin, hsCRP and Hcy respectively.

Comparison of Median Values of the Markers
(i) Mann-Whitney Test

This is a non-parametric (the data does not need to be normally distributed) which was used to test if the median values of two markers are significantly different. Minitab ranks all the data from both sets of data in order, assigning 1 to the lowest up to 200 for the highest. The software then adds up the rank-score for the two groups to be compared and reports the "P" value which indicates the chance that random sampling would result in medians as far apart as that observed in the experiment.

Calprotectin, hsCRP and Hcy median values were compared to CS split into case and control groups and the Mann-Whitney test was used to test for significance.
(ii) ROC-Curves for Calprotectin and Calcium Score The ability of a test to discriminate diseased cases from normal cases can be evaluated using Receiver Operating Characteristic (ROC) curve analysis. ROC curve analysis was used for both calprotectin and hsCRP and as a comparison of the two markers.

The ROC curves were produced using 11 cut-off limits for calculation of the sensitivity (y-axis) and the 1-specificity (x-axis). The data from the control and the case groups were pooled together and ranked from lowest to highest value. Analysis was performed on the total population and on the male population. The areas under the ROC curves were calculated using the trapezoidal rule.

Results
Summary Statistics for Calprotectin

Figure 1:
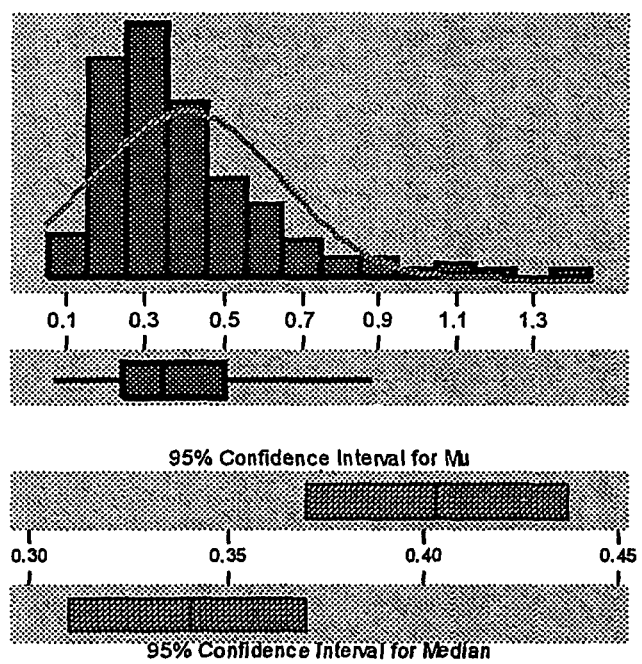
FIG. 1 is the distribution curve for calprotectin in the 200 subjects tested. The summary statistics for FIG. 1 are.

FIG. 1 shows the distribution curve for all 200 subjects tested.

Table 1 below shows the summary statistics for calprotectin in the control and the case groups. The median calprotectin concentration in the control group is 0.31 mg/L compared to 0.38 mg/L in the case group. The median calprotectin concentration is 0.31 mg/L for the males and 0.30 mg/L for the females in the control group. In the case group the median calprotectin concentration for males is 0.39 mg/L compared to 0.31 mg/L for females.

TABLE 1

Summary statistics for Calprotectin

| | Calprotectin | | | | | |
|---|---|---|---|---|---|---|
| | Controls | | | Cases | | |
| | All | Females | Males | All | Females | Males |
| N | 100 | 59 | 41 | 100 | 15 | 85 |
| SD | 0.228 | 0.232 | 0.225 | 0.503 | 0.202 | 0.537 |

TABLE 1-continued

Summary statistics for Calprotectin

| | Calprotectin | | | | | |
|---|---|---|---|---|---|---|
| | Controls | | | Cases | | |
| | All | Females | Males | All | Females | Males |
| 95% CI for median | 0.28-0.34 | 0.28-0.33 | 0.27-0.39 | 0.34-0.43 | 0.19-0.47 | 0.34-0.45 |
| Median (mg/L) | 0.31 | 0.30 | 0.31 | 0.38 | 0.31 | 0.39 |
| Min (mg/L) | 0.09 | 0.09 | 0.11 | 0.07 | 0.08 | 0.07 |
| Max (mg/L) | 1.37 | 1.37 | 1.36 | 4.85 | 0.73 | 4.85 |

Summary Statistics for Calcium Score

FIG. 2 shows the distribution curve for all 200 subjects tested.

Table 2 below shows the summary statistics for EBCT calcium score in the control and case groups. The median calcium score in the control group is 0 compared to 259 in the case group. The median calcium score is 0 for both females and males in the control group and 315 and 256, respectively, in the case group.

TABLE 2

Summary statistics for Calcium score

| | Calcium score | | | | | |
|---|---|---|---|---|---|---|
| | Controls | | | Cases | | |
| | All | Females | Males | All | Females | Males |
| N | 100 | 59 | 41 | 100 | 15 | 85 |
| SD | 5.6 | 0.7 | 8.7 | 474.7 | 365.1 | 493.3 |
| 95% CI for median | 0-0 | 0-0 | 0-0 | 313.5-215.0 | 174.8-538.0 | 300.4-207.5 |
| Median | 0 | 0 | 0 | 259 | 315 | 256 |
| Min | 0 | 0 | 0 | 100 | 100 | 100 |
| Max | 56 | 5 | 56 | 2794 | 1507 | 2794 |

Summary Statistics for hsCRP

FIG. 3 shows the distribution curve for all 200 subjects tested.

Table 3 below shows the summary statistics for hsCRP in the control and case groups. The median hsCRP in both the control group and the case group is 1.2 mg/L. The median hsCRP is 1.6 mg/L for females and 0.7 mg/L for males in the control group and 1.3 mg/L and 1.1 mg/L, respectively, in the case group.

TABLE 3

Summary statistics for hsCRP

| | hsCRP | | | | | |
|---|---|---|---|---|---|---|
| | Controls | | | Cases | | |
| | All | Females | Males | All | Females | Males |
| N | 100 | 59 | 41 | 100 | 15 | 85 |
| SD | 6.63 | 8.36 | 1.53 | 12.70 | 3.16 | 13.71 |
| 95% CI for median | 0.79-1.47 | 1.36-2.74 | 0.56-0.97 | 0.94-1.56 | 0.65-2.53 | 0.89-1.59 |
| Median (mg/L) | 1.17 | 1.59 | 0.68 | 1.23 | 1.28 | 1.11 |
| Min (mg/L) | 0.15 | 0.15 | 0.15 | 0.17 | 0.34 | 0.17 |
| Max (mg/L) | 62.1 | 62.1 | 9.29 | 120.0 | 11.9 | 120.0 |

Summary Statistics for Hcy

FIG. 4 shows the distribution curve for all 200 subjects tested.

Table 4 below shows the summary statistics for Hcy in the control and case groups. The median Hcy concentration in the control group is 7.5 μmol/L compared to 8.5 μmol/L in the case group. The median Hcy concentration is 7.15 μmol/L for females and 8.55 mol/L for males in the control group and 7.35 μmol/L and 8.55 μmol/L respectively in the case group.

TABLE 4

Summary statistics for Hcy

| | Hcy | | | | | |
|---|---|---|---|---|---|---|
| | Controls | | | Cases | | |
| | All | Females | Males | All | Females | Males |
| N | 100 | 59 | 41 | 100 | 15 | 85 |
| SD | 1.94 | 1.58 | 2.18 | 6.03 | 2.18 | 6.46 |
| 95% CI for median | 7.7-8.5 | 7.1-7.9 | 8.1-9.5 | 8.1-10.5 | 6.8-9.2 | 8.1-10.9 |
| Median (μmol/L) | 7.5 | 7.1 | 8.5 | 8.5 | 7.3 | 8.5 |
| Min (μmol/L) | 5.3 | 5.3 | 5.3 | 5.1 | 5.1 | 5.2 |
| Max (μmol/L) | 14.7 | 11.8 | 14.7 | 65.8 | 12.4 | 65.8 |

Comparison between Calcium Score and Calprotectin, hsCRP, Hcy (i) Chi-squared Test Using Minitab, chi-squared tables were performed (see table 5 below). This test compares expected distributions between sets of data (assuming a random distribution) and those observed. The significance value is a measure of the degree to which the data is not randomly distributed. For example, considering the data for calprotectin positive it would be expected that there would be an even spilt between calcium positive and negative (i.e. 30.5 expected in both columns). The observed split, however, is 22 negative and 39 positive indicating a tendency for the calprotectin positives to co-vary with the calcium positives.

Minitab provides an overall measure of the significance of these differences (both agreement and disagreement) and in this case P is 0.009. Thus there is a significant co-variation of calcium with calprotectin.

TABLE 5

Chi-Square comparison of Calprotectin versus Calcium score

| | | Calcium (co 100) | | |
|---|---|---|---|---|
| Calprotectin (co 0.45 mg/L) | | Negative (N) | Positive (N) | All (N) |
| Negative | Obs | 78 | 61 | 139 |
| | Exp | 69.5 | 69.5 | 139 |
| Positive | Obs | 22 | 39 | 61 |
| | Exp | 30.5 | 30.5 | 61 |
| All | Obs | 100 | 100 | 200 |
| | Exp | 100 | 100 | 200 |

An analogous comparison was made between calprotectin and hsCRP (see Table 6 below).

TABLE 6

Chi-Square comparison of Calprotectin versus hsCRP (P = 0)

| | | hsCRP (co 1.69 mg/L) | | |
|---|---|---|---|---|
| Calprotectin (co 0.45 mg/L) | | Negative (N) | Positive (N) | All (N) |
| Negative | Obs | 100 | 39 | 139 |
| | Exp | 88.96 | 50.04 | 139 |

TABLE 6-continued

Chi-Square comparison of Calprotectin versus hsCRP (P = 0)

| | | hsCRP (co 1.69 mg/L) | | |
|---|---|---|---|---|
| Calprotectin (co 0.45 mg/L) | | Negative (N) | Positive (N) | All (N) |
| Positive | Obs | 28 | 33 | 61 |
| | Exp | 39.04 | 21.96 | 61 |
| All | Obs | 128 | 72 | 200 |
| | Exp | 128 | 72 | 200 |

(ii) Odds Ratio

Odds ratios can be derived from tables 5 and 6 and give a measure of how far the values observed deviate from the expected. If the expected agreement figures are multiplied together and divided by the product of the disagreement expected figures a value of 1 should be obtained.

Taking the data in Table 6, for instance, the odds ratio on the expected values is 1: (88.96×21.96)/(50.04×39.04) =1953.64/1953.6=1.

The odds ratio observed in this table is: (100×33)/(39×28)=3300/1092=3.02.

The further the odds ratio from 1 the more pronounced the co-variation; an odds ratio of 3 is significant.

The results of an odds ratio analysis carried out on the co-variance data obtained from the study are shown in Table 7.

TABLE 7

Summary of Odds-Ratio findings

| | Odds ratio | | |
|---|---|---|---|
| Risk markers | | | |
| (N1#pos, N2#neg) | Calcium | Calprotectin | CRP |
| Calcium Score (co 100) N1 = 100, N2 = 100 | — | — | — |

TABLE 7-continued

Summary of Odds-Ratio findings

| Risk markers (N1#pos, N2#neg) | Odds ratio | | |
|---|---|---|---|
| | Calcium | Calprotectin | CRP |
| Calprotectin (co 0.45 mg/L) N1 = 61, N2 = 139 | 2.27 | — | — |
| CRP (co 1.69 mg/L) N1 = 72, N2 = 128 | 1.00 | 3.02 | — |
| Hcy (co 12 μmol/L) N1 = 11, N2 = 189 | 1.21 | 1.32 | 1.52 |
| (co 10 μmol/L) N1 = 42, N2 = 158 | 1.63 | 1.55 | 1.12 | co = cut off

A high odds ratio indicates a high degree of co-variation between the tests. It can be seen from Table 7 that the test for calprotectin gives the highest odds ratio to calcium score and therefore it can be deduced that calprotectin has the highest degree of covariance with calcium score out of calprotectin, CRP and homocysteine.

Additionally, calprotectin gives a high odds ratio with CRP, another marker for CVD.

Chi-Squared Analysis using Minitab

A chi-squared test on the above data, using the same cut-offs as the odds-ratio test, showed significant (P 0.009) agreement between the calcium score and calprotectin results. In contrast, neither the test for CRP nor the test for homocysteine showed any significant co-variance with calcium score.

Significant agreement (P 0.000) was also found between calprotectin and CRP.

Comparing Median Values (i) Mann-Whitney Test

FIG. 5 shows the dot-plot for the distribution of calprotectin between the calcium positive and the calcium negative results.

The median values for the two groups are 0.310 mg/L for the negative calcium and 0.375 mg/L for the positive calcium. Mann-Whitney provides that the sum of the ranks for the negative calcium is 912 and 1108 for calcium negative and yields a P value of 0.0113.

A Mann-Whitney analysis to test for significant increases in the medians of each of calprotectin, CRP, and homocysteine concentration in the high (CS>100) and low (CS<100) calcium score groups was also carried out on the above data. The results showed that the median values for calprotectin and homocysteine concentration were significantly raised in the high calcium group (P=0.0112 and 0.0037 respectively) whereas CRP did not show any significant difference in either group (see Table 8 below).

TABLE 8

Comparison of median values of Calprotectin and Hcy

| | Median value in low CS group | Median value in high CS group | P value |
|---|---|---|---|
| Calprotectin | 0.3 mg/L | 0.4 mg/L | 0.0112 |
| Homocysteine | 7.5 μmol/L | 8.5 μmol/L | 0.0037 |

(ii) ROC Analyses and Curves

FIGS. 6 and 7 shows the ROC curves for calprotectin and hsCRP for all subjects and the male population. Table 9 below shows the area under the ROC curves.

TABLE 9

Area under the ROC curves

| Group | Calprotectin | hsCRP |
|---|---|---|
| All subjects | 0.604 | 0.524 |
| Male subjects | 0.622 | 0.502 |

Agreement Rate Against Calcium Score

The accuracy of each of the calprotectin, CRP and homocysteine (Hcy) tests at the cut-off levels (Hcy co 12 μmol) in Table 7 as a test for potential to CVD was also assessed assuming that a calcium score >100 is reflective of high risk to CVD.

The results of the analysis are shown in Table 10.

TABLE 10

| Calprotectin & CRP incorrect | Calprotectin correct & CRP incorrect | Calprotectin incorrect & CRP correct | Calprotectin & CRP correct |
|---|---|---|---|
| 58 29% | 42 21% | 25 12.5% | 75 37.5% |

| Calprotectin & Hcy incorrect | Calprotectin correct & Hcy incorrect | Calprotectin incorrect & Hcy correct | Calprotectin & Hcy correct |
|---|---|---|---|
| 59 29.5% | 40 20% | 24 12% | 77 38.5% |

Agreement rate against calcium for calprotectin = 58.5% (42 + 75/200)
Agreement rate against calcium for CRP = 50% (25 + 75/200)
Agreement rate against calcium for homocysteine = 50.5% (24 + 77/200)

The invention claimed is:

1. A direct turbidimetric assay method for the determination of calprotectin at concentrations of 0.5 to 50 mg/L in a calprotectin-containing body fluid, said method comprising the steps of:
    (a) obtaining a calprotectin-containing liquid sample of, or derived from, said body fluid, wherein said liquid sample comprises calprotectin at a concentration of 0.5 to 50 mg/L;
    (b) contacting said liquid sample of said body fluid with anti-calprotectin antibodies or antibody fragments, to bind said calprotectin, wherein said anti-calprotectin antibodies or antibody fragments are egg polyclonal antibodies or fragments thereof having a population of calprotectin binding sites and are immobilised by binding or coupling, either directly or indirectly, to nanoparticles to form antibody or antibody fragment coated nanoparticles; and
    (c) assessing the calprotectin content in said contacted liquid sample by turbidimetry,
    wherein the diameter of the antibody or antibody fragment coated nanoparticles is 65-140 nm, wherein increasing opacity correlates with increasing calprotectin concentration; and wherein said assay is capable of measuring calprotectin with precision in samples having calprotectin concentrations throughout the range of 0.5-50 mg/L.

2. The method of claim 1 wherein the diameter of the antibody or antibody fragment coated nanoparticles is 75-120 nm.

3. The method of claim 2, wherein the nanoparticles consist of polyethylene.

4. The method of claim 2, wherein the nanoparticles consist of gold.

5. The method of claim 2, wherein the nanoparticles consist of glass.

6. The method of claim 1 wherein said nanoparticles are substantially all of the same size.

7. The method of claim 1 wherein an opacity enhancer is added in between steps (b) and (c).

8. The method of claim 1 wherein said body fluid is selected from blood, serum, plasma, urine, cerebrospinal fluid, oral fluid, synovial fluid or empyema fluid.

9. The method of claim 1 performed as an automated assay.

10. The method of claim 1 wherein said nanoparticles are monodisperse.

11. The method of claim 1, wherein the body fluid is treated with calcium or ions or another alkaline earth metal prior to being used in the assay method.

12. The method of claim 11, wherein sufficient calcium or ions of another alkaline earth metal is added to the body fluid to saturate the calcium binding sites of calprotectin.

13. A direct turbidimetric assay method for the determination of calprotectin at concentrations of 0.5 to 50 mg/L in a calprotectin-containing body fluid, said method comprising the steps of:

(a) obtaining a calprotectin-containing liquid sample of, or derived from, said body fluid, wherein said liquid sample comprises calprotectin at a concentration of 0.5 to 50 mg/L;

(b) contacting said liquid sample of said body fluid with a composition consisting essentially of anti-calprotectin antibodies or antibody fragments immobilized by binding or coupling, either directly or indirectly, to nanoparticles to form antibody or antibody fragment coated microparticles; wherein said anti-calprotectin antibodies or antibody fragments are egg polyclonal antibodies or fragments thereof having a population of calprotectin binding sites; and (c) assessing the calprotectin content in said contacted liquid sample by turbidimetry, wherein the diameter of the antibody or antibody fragment coated nanoparticles is 65-140 nm, and wherein increasing opacity correlates with increasing calprotectin concentration; and wherein said is capable of measuring calprotectin with precision in samples having calprotectin concentrations throughout the range of 0.5-50 mg/L.

* * * * *